US009237905B2

(12) United States Patent
Chase et al.

(10) Patent No.: US 9,237,905 B2
(45) Date of Patent: Jan. 19, 2016

(54) MEDICAL INSTRUMENT FOR INSERTION INTO A BODY REGION OF A SUBJECT

(71) Applicants: Ronald M. Chase, Apopka, FL (US); William A. Baker, Cambridge, NY (US)

(72) Inventors: Ronald M. Chase, Apopka, FL (US); William A. Baker, Cambridge, NY (US)

(*) Notice: Subject to any disclaimer, the term of this patent is extended or adjusted under 35 U.S.C. 154(b) by 0 days.

(21) Appl. No.: 13/959,002

(22) Filed: Aug. 5, 2013

(65) Prior Publication Data
US 2014/0148838 A1 May 29, 2014

Related U.S. Application Data

(60) Provisional application No. 61/730,565, filed on Nov. 28, 2012.

(51) Int. Cl.
*A61B 17/34* (2006.01)
*A61B 17/3209* (2006.01)
*A61M 5/32* (2006.01)

(52) U.S. Cl.
CPC .......... *A61B 17/3401* (2013.01); *A61B 17/3209* (2013.01); *A61B 17/3421* (2013.01); *A61M 5/3286* (2013.01)

(58) Field of Classification Search
CPC ............ A61B 17/06066; A61B 17/3401; A61M 5/3286; A61M 5/32; A61M 5/329
USPC .......... 600/567, 566, 564; 606/223, 185, 167; 604/264, 174, 164.06, 272
See application file for complete search history.

(56) References Cited

U.S. PATENT DOCUMENTS

| | | | | |
|---|---|---|---|---|
| 2,192,728 A * | 3/1940 | Dewas | ...................... | D03J 5/00 139/448 |
| 4,524,771 A * | 6/1985 | McGregor | ....... | A61B 17/06066 223/102 |
| 4,651,752 A * | 3/1987 | Fuerst | ................ | A61B 10/0266 600/567 |
| 4,708,147 A * | 11/1987 | Haaga | ........................... | 600/566 |
| 4,781,202 A * | 11/1988 | Janese | .......................... | 600/567 |
| 5,178,628 A * | 1/1993 | Otsuka | ............. | A61B 17/06066 163/5 |
| 5,342,397 A * | 8/1994 | Guido | .......................... | 606/222 |
| 5,512,037 A * | 4/1996 | Russell | .............. | A61B 17/0218 600/201 |
| 5,554,167 A * | 9/1996 | Young | ................ | A61B 17/3417 604/274 |
| 5,730,749 A * | 3/1998 | Battenfield | ................... | 606/167 |
| 5,895,401 A * | 4/1999 | Daum | .................... | G01R 33/28 606/167 |
| 7,070,583 B1 * | 7/2006 | Higuchi et al. | ............... | 604/274 |
| 7,153,316 B1 * | 12/2006 | McDonald | .................... | 606/166 |
| 8,088,081 B2 * | 1/2012 | Field | ..................... | A61B 10/02 600/567 |

(Continued)

*Primary Examiner* — Kevin C Sirmons
*Assistant Examiner* — William Carpenter

(57) ABSTRACT

In one embodiment, the invention includes a medical instrument for insertion into a subject including an elongate body which includes a proximal end and a distal end, a broad face, a narrow face, a lateral side and a counter-lateral side, said faces and sides defining a trapezoid shape along the length of the elongate body. The broad and narrow faces are generally parallel to one another and the lateral and counter-lateral sides each connect between the broad and narrow faces. The distal end of the instrument includes a cutting edge and is provided for insertion into the subject, wherein an incision made in a target area of the subject results in a linear penetration in the target area. An aperture may be disposed at or near the distal end of the medical instrument.

14 Claims, 14 Drawing Sheets

(56) References Cited

U.S. PATENT DOCUMENTS

| | | | |
|---|---|---|---|
| 8,366,748 B2* | 2/2013 | Kleiner | A61B 17/025 606/279 |
| 8,556,924 B2* | 10/2013 | Liu | A61B 17/3421 606/185 |
| 8,568,334 B2* | 10/2013 | Field | A61B 10/0266 600/567 |
| 8,574,167 B2* | 11/2013 | Smith | A61B 10/0275 600/562 |
| 2004/0127941 A1* | 7/2004 | Cunningham et al. | 606/223 |
| 2004/0186501 A1* | 9/2004 | Su | A61M 37/0076 606/185 |
| 2006/0030785 A1* | 2/2006 | Field et al. | 600/567 |
| 2006/0100654 A1* | 5/2006 | Fukuda et al. | 606/181 |
| 2008/0281224 A1* | 11/2008 | Johnson | A61B 10/0275 600/567 |
| 2009/0216220 A1* | 8/2009 | Hoey et al. | 606/27 |
| 2010/0023054 A1* | 1/2010 | Matsutani et al. | 606/223 |
| 2010/0145391 A1* | 6/2010 | Kleiner | 606/279 |
| 2011/0257478 A1* | 10/2011 | Kleiner et al. | 600/104 |
| 2012/0059247 A1* | 3/2012 | Speeg | A61B 8/0841 600/424 |
| 2012/0083749 A1* | 4/2012 | Kawamoto et al. | 604/239 |
| 2012/0253376 A1* | 10/2012 | Liu et al. | 606/185 |
| 2012/0289860 A1* | 11/2012 | McClellan | 600/566 |

\* cited by examiner

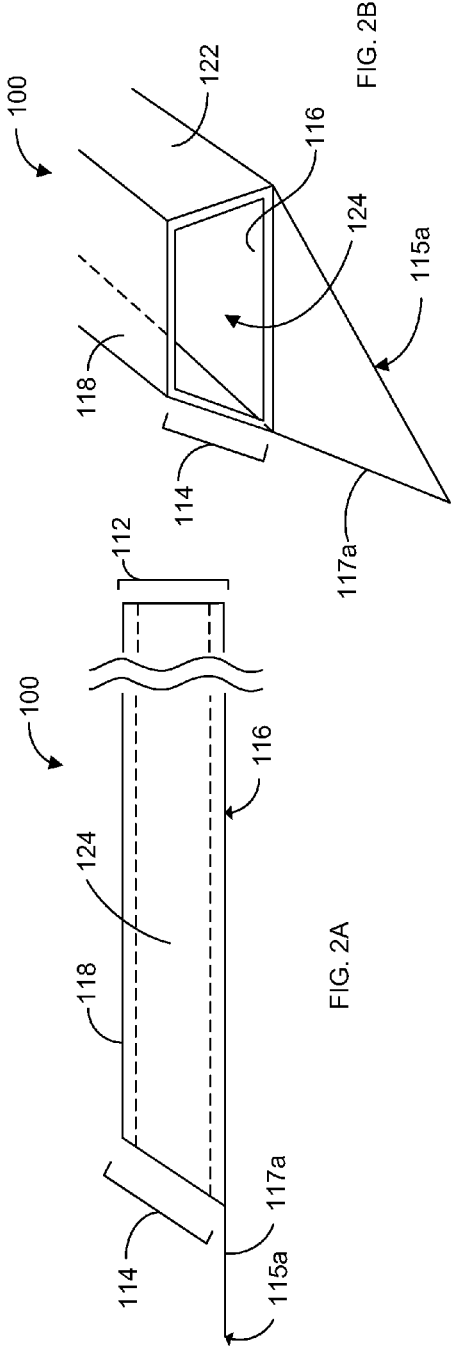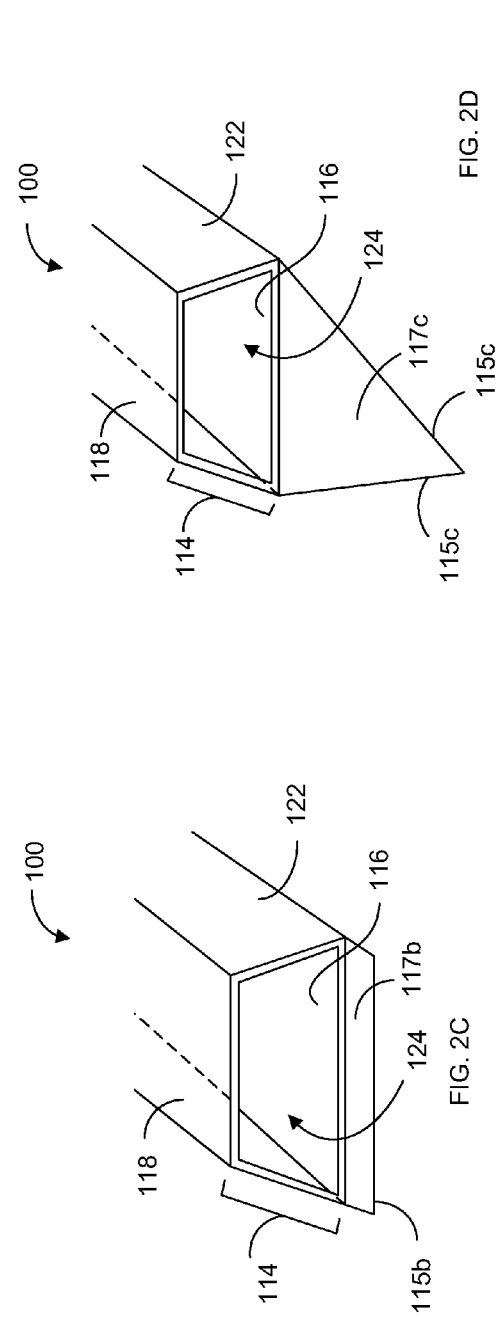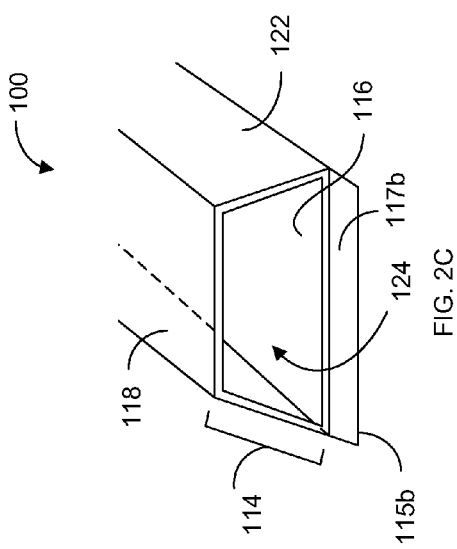

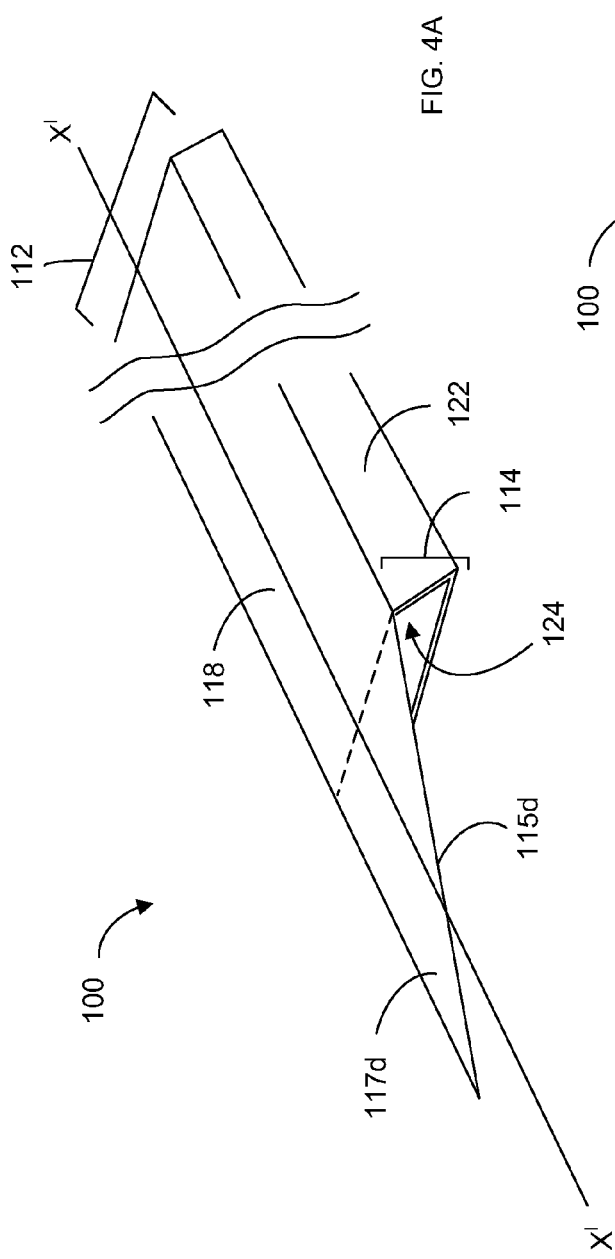
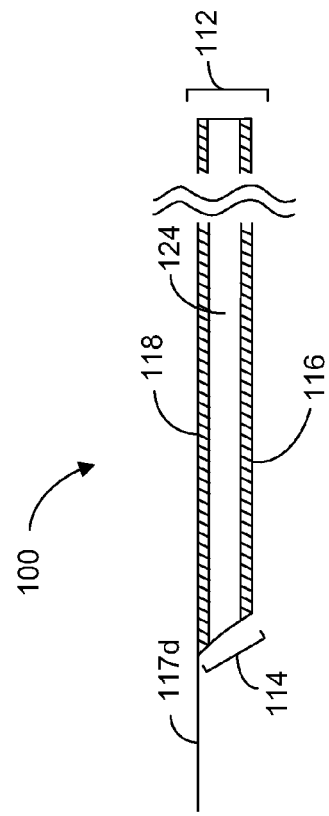

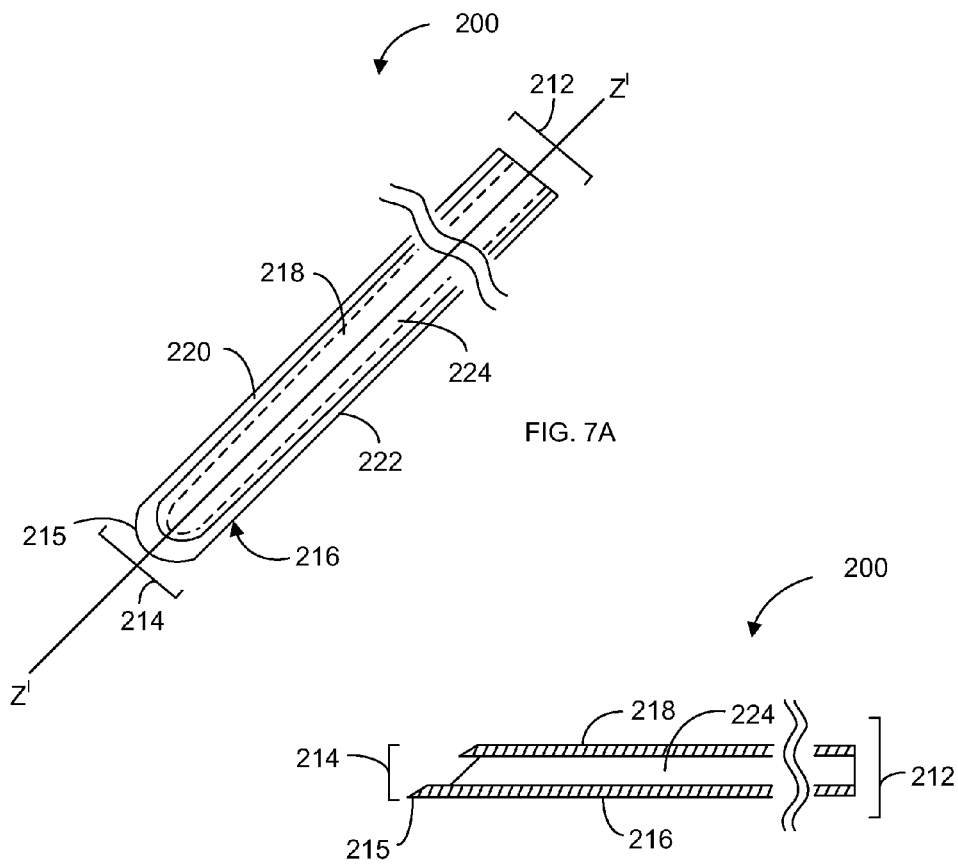
FIG. 7A
FIG. 7B
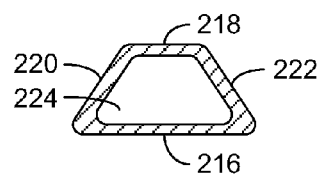
FIG. 7C

FIG. 10A
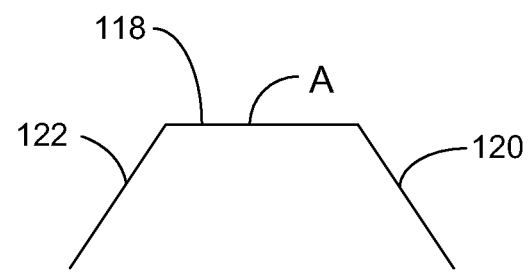
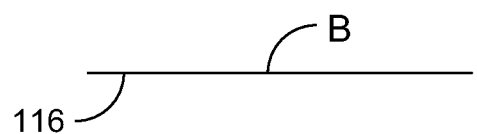
FIG. 10B
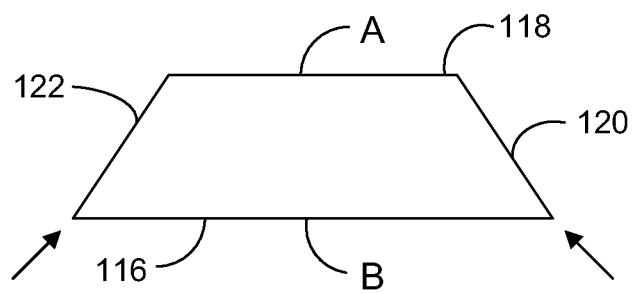
FIG. 10C

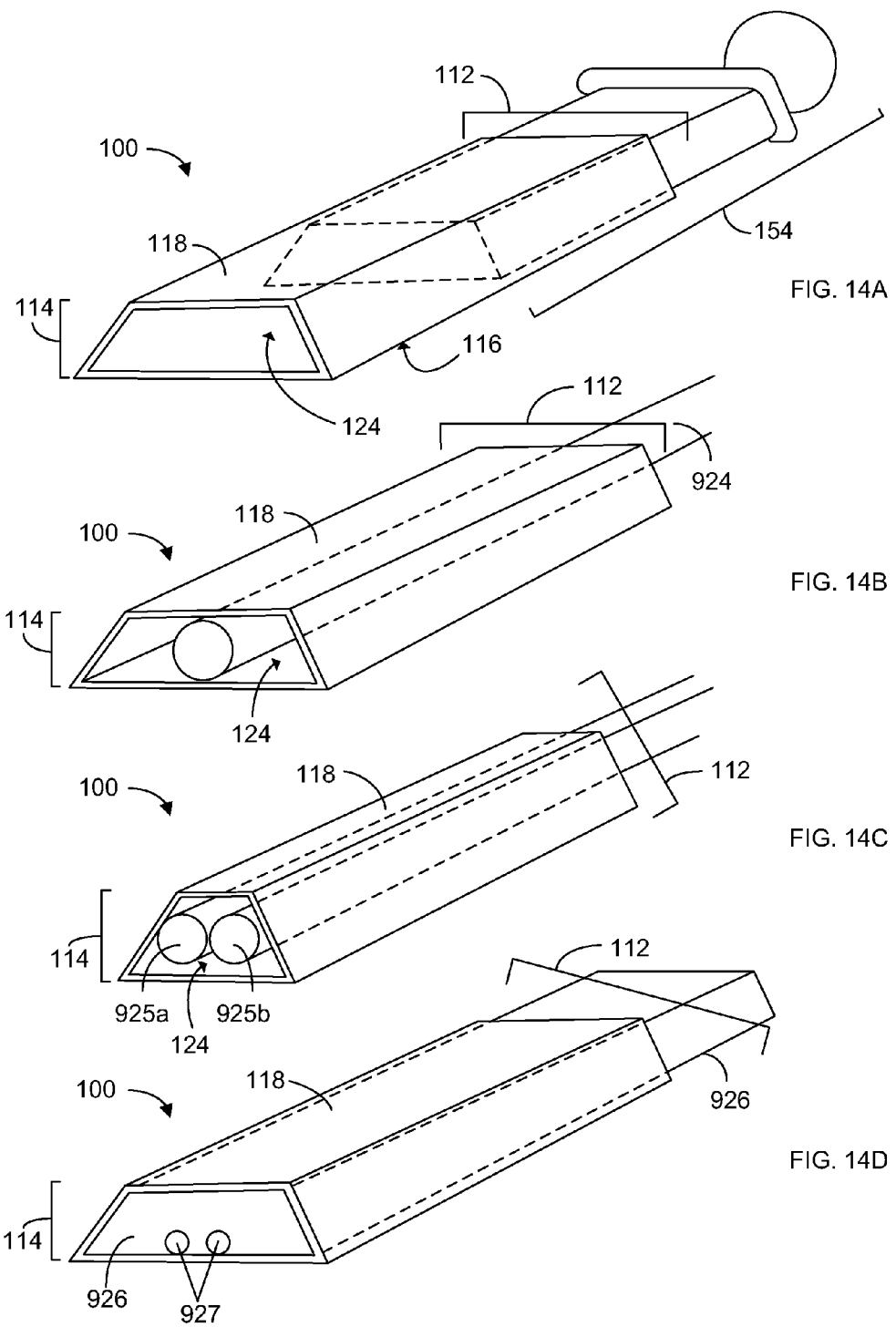

MEDICAL INSTRUMENT FOR INSERTION INTO A BODY REGION OF A SUBJECT

CROSS-REFERENCE TO RELATED APPLICATIONS

This application is related to U.S. Provisional Application No. 61/730,565 filed Nov. 28, 2012 to which priority is claimed under 35 USC 119.

BACKGROUND

For over 100 years surgeons and medical practitioners have used needles and trocars with circular tubular shafts and various round end configurations. From the advent of modern medical practice to the present, surgeons have relied on devices made from round tubular/circular materials. Round ended or circular medical instruments are typically used in most medical procedures, and are most widely available. Circular or round-ended medical instruments once introduced into and removed from a patient leave behind a puncture-type opening or wound at the access point. It is known that circular openings or wounds in the body typically heal more slowly than linear openings or linear wounds.

SUMMARY

In one embodiment, the invention includes a medical instrument for insertion into a subject of an elongate body which includes a proximal end, a distal end, a broad face, a narrow face, a lateral side and a counter-lateral side; wherein said distal end is provided for insertion into the subject. The broad face, narrow face, lateral side and counter-lateral side include a distal end and a proximal end. The broad and narrow faces are parallel to one another, and the lateral and counter-lateral sides each connect between the broad and narrow faces forming a channel, the channel extending from the proximal end to the distal end of the medical instrument, in one embodiment. In one embodiment, the channel extends through the distal end of the medical instrument. In another embodiment, the channel extends to but not through the distal end of the medical instrument. In yet a further embodiment, an aperture may be provided in the narrow, broad, counter-lateral or lateral face of the instrument, wherein the aperture may open to the channel disposed within the length of the instrument. In one embodiment, the lateral and counter-lateral sides are not parallel to one another, such that said broad face and narrow face and lateral and counter-lateral sides form a trapezoid shape along the length of the elongate body.

In a further embodiment, a medical instrument for insertion into a body of a subject is provided. Additionally, each of the broad and narrow faces may have a lateral and counter-lateral edge so specified for purposes of clarification or elaboration. In one embodiment, the broad face has a greater width than the narrow face. In a further embodiment, the medical instrument includes a cutting edge at its distal end, either at the broad or the narrow face distal end, preferably at the broad face distal end; or at both the broad and narrow faces at the distal end.

In an embodiment of the medical instrument, the broad and narrow faces are generally parallel to one another. The lateral edge of the broad face connects to the lateral edge of the narrow face by the lateral side. The counter-lateral side connects the broad and narrow faces such that the hollow elongate body is formed. In some embodiments, the lateral and counter-lateral sides are not parallel to one another and connect with the broad and narrow faces to form a trapezoidal shape there between.

In another embodiment, a method for making a quick-healing incision in a target area of a subject is provided. The method includes creating a non-puncturing, linear-type incision in the target area by inserting a medical instrument into the target area. The medical instrument is longitudinal and has a distal end and a proximal end. The instrument includes the two parallel faces (narrow and broad) and two non-parallel counter-lateral and lateral sides so as to form a trapezoid shape there between. The two parallel faces and two non-parallel sides define a channel through at least a portion of the length of the medical instrument. In some embodiments, the channel extends from the distal end to the proximal end of the instrument. The distal end can be sharpened and beveled such that a linear incision can be made in the target area of the subject using the distal end of the medical instrument. Alternatively, the distal end may include a blade portion projecting there from which includes a sharpened edge for insertion in the target area. The method further includes removing or retreating the medical instrument from the target area leaving a linear opening in the target area of the subject.

BRIEF DESCRIPTION OF THE DRAWINGS

A more particular description as stated above will be rendered by reference to specific embodiments thereof that are illustrated in the appended drawings. Understanding that these drawings depict only typical embodiments and are not therefore to be considered to be limiting of its scope, the embodiments will be described and explained with additional specificity and detail through the use of the accompanying drawings in which:

FIG. 2A provides a side view of another embodiment of a medical instrument including a blade projecting distally from a broad face of the instrument.

FIG. 2B provides a front perspective view of a portion of a medical instrument embodiment shown in the side view of FIG. 2A.

FIG. 2C provides a front perspective view of a portion of another embodiment of a medical instrument including a blade projecting distally from the broad face of the instrument.

FIG. 2D provides a front perspective view of a portion of a further embodiment of a medical instrument including a blade projecting distally from the broad face of the instrument.

FIG. 4A provides a perspective view of another embodiment of the medical instrument including a blade projecting distally from the narrow face.

FIG. 4B provides a longitudinal cross-sectional view of the embodiment of the medical instrument shown in FIG. 4A, taken at X'-X'.

FIG. 7A provides a top view of an epidural medical instrument embodiment including a rounded or curved distal end and a channel disposed between the narrow and broad faces.

FIG. 7B provides a longitudinal cross-sectional view of the epidural medical instrument embodiment of FIG. 7A, taken at Z'-Z'.

FIG. 7C provides a transverse cross-sectional view of FIG. 7A.

FIG. 10A provides a first portion (A) and a second portion (B) of a medical instrument construction.

FIG. 10B provides a view of the first portion (A) being manipulated such that its ends are bent to meet the second portion (B).

FIG. 10C provides a view of the medical instrument formed by the first portion and second portions of FIGS. 10A-10B, wherein the points at which (A) contacts (B) are secured to one another to form the medical instrument embodiment, a trapezoidal shape.

FIG. 14A provides a perspective view of a medical instrument according to an embodiment of the invention wherein a stylet is disposed within the medical instrument.

FIG. 14B provides a perspective view of a medical instrument according to an embodiment of the invention wherein a circular conduit or instrument is inserted from the proximal end through to the distal end of the medical instrument.

FIG. 14C provides a perspective view of a medical instrument according to an embodiment of the invention, wherein multiple conduits or instruments are inserted from the proximal end through to the distal end of the medical instrument.

FIG. 14D provides a perspective view of a medical instrument according to an embodiment of the invention, wherein a trapezoidal-shaped device comprising multiple openings is inserted into the medical instrument.

Figure 1A:
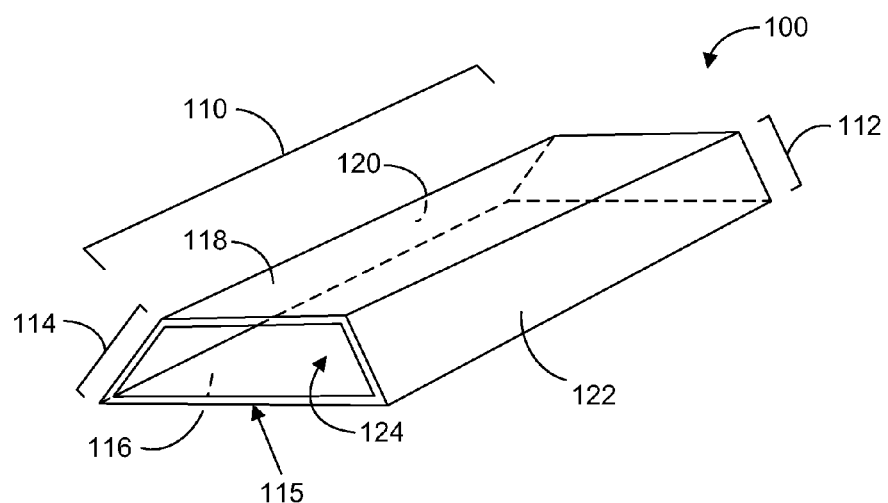
FIG. 1A provides a perspective view of a medical instrument according to an embodiment of the invention.

It is noted that the wavy lines in the body of the instrument are not a feature of the instrument. They are intended to represent that the instrument body has a length that spans between where the wavy lines are shown, such length being predetermined depending on the intended use of the instrument.

DETAILED DESCRIPTION

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item. The modifier "about" used in connection with a quantity is inclusive of the stated value and has the meaning dictated by the context. It is to be noted that all ranges disclosed within this specification are inclusive and are independently combinable.

DEFINITIONS

The terms "medical instrument" or "instrument" can be used interchangeably herein. In some embodiments, the medical instrument may be a needle, a blade, or an injection device. In other embodiments, the medical instrument may be a trocar, an epidural needle, or a spinal needle or a spinal trapezoid flat blade needle, for example. The terms "body" and "shank" may also be used interchangeably throughout this description.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human.

The inventors have identified herein, a medical instrument having a structure which provides particular advantages to both medical professionals and patients alike. The principal design attribute of a medical instrument as described herein, for example, for any subcutaneous invasion to conduct any medical procedure is better wound healing by primary intention where there is little or no tissue loss and the wound is held together by a clot or adherence of the edges of the wound or incision, in some instances. The epithelial cells migrate to the clot faster and eventually cover the wound with minimal scar tissue. By contrast, puncture wounds made by conventional circular needles and Trocars of the prior art may heal by secondary intention.

A puncture wound heals more slowly because tissue is removed or displaced leaving a larger open area prone to infection and covered with granulation tissue that bleeds easily. Granulation tissue subsequently causes skin contraction as more epithelial cells migrate to the wound area and a larger scar tissue results. Furthermore, additional benefits result from the structural characteristics of the invention as claimed herein such as an increase in laminar flow through first and/or second conduits of the instrument due to the rectangular and/or trapezoidal shape of the distal end of the instrument and the straight sides of the instrument 100 in contrast to the circular conduits currently in use in the prior art which are susceptible to increased turbulence as fluid flows through the circular conduit.

As shown in FIG. 1A, a perspective view of an embodiment of a medical instrument 100 is provided, which includes the medical instrument 100 for insertion into a subject including an elongate body 110, a proximal end 112 and a distal end 114, a broad face 116, a narrow face 118, a lateral side 120 and a counter-lateral side 122, wherein said distal end 114 is provided for insertion into a target area of a subject. The broad and narrow faces 116, 118 are generally parallel to one another, and the lateral and counter-lateral sides 120, 122 each connect between a narrow face 118 and a broad face 116. The broad face 116, narrow face 118, lateral side 120 and counter-lateral side 122 together form a trapezoidal shape extending from the proximal end 112 to the distal end 114 along the length of the elongate body 110 of the medical instrument 100. In the embodiment shown in FIG. 1A, the edge formed at the distal end 114 of the broad face 116 is a cutting edge 115 which is used to create an incision in a target area of a subject.

The distal ends 114 of many of the embodiments of the instrument 100 described herein are beveled, such that the distal end 114 of one of the broad face 116 or the narrow face 118 extends distally past the other of the broad face 116 or the narrow face 118 as can be seen in the longitudinal cross-sectional views provided herein. In the embodiment of FIG. 1A, the broad face 116 extends distally past the narrow face 118, such that the distal end 114 of the instrument 100 is sloped from the distal end of the narrow face 118 in a more proximal position to the distal end of the broad face 116 in a more distal position. In use, in any of the embodiments described herein, the instrument 100 may be inserted into a patient target area with the narrow face 118 in a superior position to the broad face 116 or vice versa, or with the lateral side 120 superior to the counter-lateral side 122, or vice versa.

Figure 1B:
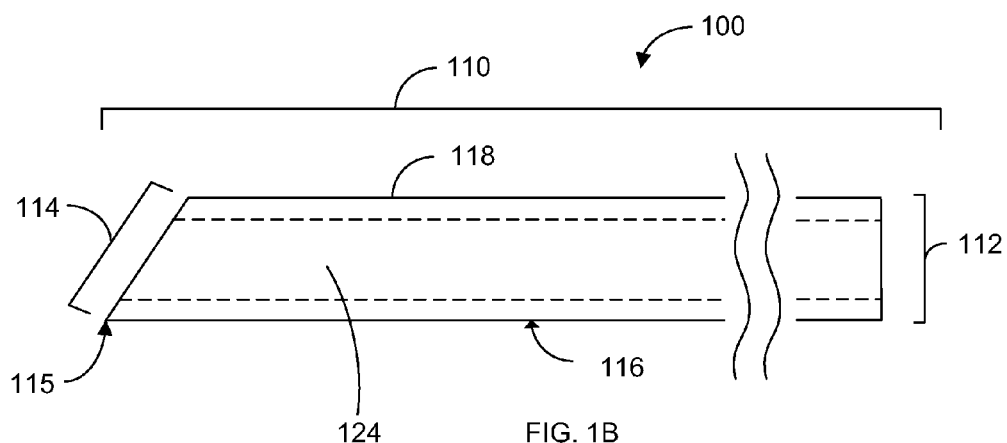
FIG. 1B provides a side view of the of the medical instrument embodiment of FIG. 1A.

FIG. 1B provides a side view of the medical instrument embodiment 100 of FIG. 1A, wherein the beveled distal end 114 is shown and a channel 124 can be seen as extending from the proximal end 112 to the distal end 114 of the elongate body 110 of the instrument 100. The cutting edge 115 is also shown in FIG. 1B. The proximal end 112 is shown beveled similar to proximal end 114. Those skilled in the art would readily appreciate in view of the teachings herein that the proximal end may or may not have a beveled edge, such as that shown and described with respect to distal end 114. As shown in FIG. 1B and other figures discussed herein, the proximal end 112 is shown as being beveled, but this is merely one configuration and is not to be interpreted as limiting. A transverse cross-sectional view of the medical instrument 100 of FIGS. 1A-1B would reveal a trapezoidal shape created by the narrow face 118, broad face 116, counter-lateral side 122 and lateral side 120, extending from the proximal end 112 to the distal end 114 of the instrument 100. The channel 124 is also provided in a trapezoid shape.

Figure 1C:
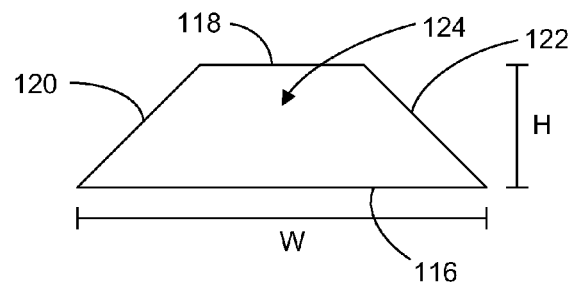
FIG. 1C provides a cross-sectional view of the medical instrument embodiment of FIG. 1A, providing an example of the height "H" to width "W" ratio of a cross section of the instrument.

FIG. 1C provides a cross-sectional view of the medical instrument embodiment 100 of FIG. 1A, illustrating an example of the height "H" to width "W" ratio of a cross section of the instrument 100. The medical instrument 100 may be one of any dimensions or sizes as adapted to perform the functions as described herein, depending on the desired implementation of the instrument. In one embodiment, the height to width ratio (i.e. where height is the distance between the narrow face 118 and the broad face 116, and width is the distance between the lateral side 120 and the counter-lateral side 122) of the elongate body ranges from 1:2 to 1:15. The elongate body may taper from the distal end 114 to the proximal end 112, or vice versa, and may thus include a varying width to height ratio there through. In a further embodiment, the height to width ratio of the elongate body is in a ratio of 1:2, 1:3, 1:4, 1:5, 1:6, 1:7, 1:8, 1:9, 1:10, 1:11, 1:12, 1:13, 1:14, or 1:15.

Unlike conventional circular instruments used to make circular openings or punctures in a subject body or body cavity, the flat and/or trapezoidal shaped distal end 114 of the medical instrument 100 causes a decrease in patient trauma during and after a non-puncture incision by the instrument into the target area of the patient. By making a linear-type incision, such as that which is made with the cutting edge 115 in this embodiment, less damage is caused to the tissues involved in the procedure, which in turn decreases recovery time of the patient following the procedure. Because the instrument 100 produces an incision with minimal shredding of the tissues and less bleeding, it promotes faster healing of the wound after the treatment procedure is complete.

While an incision made using the instrument 100 is longer than if made using a round needle (i.e., the round diameter is greater), the instrument of the subject invention is capable of displacing an equivalent volume because of its width, and it also reduces the trauma to the patient due to its elongated linear incision. While the cross-sectional views of the medical instrument 100 provided herein would demonstrate a trapezoidal shape from proximal to distal end, or at any point there between, in an alternative embodiment, the lateral side 120 and counter-lateral side 122 may be parallel to one another, which would provide for a square-shaped cross-section of the instrument. A further benefit of medical instrument embodiment 100 described herein is the rigidity caused by the cross sectional trapezoidal shape that will cause the instrument to act like an I-beam, in one example, thus restricting wandering of the distal end 114 during use. Thus the trajectory of the instrument 100 is more accurate than a circular needle body which can wander because of its greater flexibility.

Additionally, another advantage of the instrument embodiments described herein is the greater ease of incising between ribs, vertebrae, and other structures, causing less damage to surrounding tissues and more accurate placement of the distal end of the instrument 100 due to the structural characteristics of the embodiments herein.

The elongate body 110 of the medical instrument 100 may include a channel 124 extending there through, in some embodiments. The broad face 116 and narrow face 118 of the trapezoid are generally parallel, and may include, for example, widths in 2:1 ratio, in one embodiment, or another such ratio which is contemplated herein. The two adjacent sides, the lateral side 120 and counter-lateral side 122 of the elongate body 110 are angled and connect between the narrow and broad faces 118, 116, forming a trapezoid shape there between. In some embodiments, the lateral 120 and counter-lateral 122 sides may be parallel. In a further embodiment, the lateral and/or counter-lateral sides 120, 122 may include a concave or convex, or be closer to an elliptical shape as shown in FIGS. 8A-E (as will be discussed in greater detail below).

FIG. 2A provides a side view of an embodiment of a medical instrument 100 comprising a sloped distal end 114, a channel 124 extending from the distal end 114 to the proximal end 112, and a cutting edge 115a provided on a blade portion 117a projecting from the distal end 114 of the broad face 116. The narrow face 118 is generally parallel to the broad face 116. The blade portion 117a is more clearly seen in the perspective view of the instrument embodiment 100 of FIG. 2B, where it extends distally from the distal end 114 of the broad face 116. The blade portion 117a can be used to create an incision in a target area of a patient. The shape and dimensions of the blade portion 117a are dependent upon the size and shape of the distal end 114 of the instrument 100. However, the blade portion 117a differs from blade portion 117c (in FIG. 2D), as the two sides of the blade portion 117a which project from the instrument 100 are not equal in length. FIG. 2B provides a perspective view of an embodiment of the medical instrument 100 wherein the blade portion 117a is shaped as an isosceles triangle, with cutting edge 115a.

FIG. 2C provides a perspective view of an embodiment of the medical instrument 100, wherein the blade portion 117b is a projection of the broad face 116 distal end 114 of the instrument 100 with cutting edge 115b and the blade portion 117b is a non-triangular shaped blade portion 117b. FIG. 2D provides a perspective view of a medical instrument embodiment 100, wherein the blade portion 117c is shaped as an equilateral triangle having sides (i.e., cutting edges 115c) of equal length which protrude or extend distally from the broad face 116 of the instrument 100. The blade portion 117a, b, c in FIGS. 2A,B,C, and D may take any shape which will provide an incision into a target area of a patient, including but not limited to the shapes and sizes described in the examples herein.

The distal end 114 is beveled or sharpened into a distal scalpel cutting edge 115a-c by processes known currently to the industry and includes the blade portions 117a-c described herein. The distal end of the narrow face 118 is proximal with respect to the distal end of the broad face 116. The distal end 114 of the lateral side 122 and the counter-lateral side 120 (seen in FIG. 1A) of the instrument 100 are not parallel to one another as disposed between the generally parallel broad 116 and narrow faces 118, in an embodiment. The distal ends 114 of the counter-lateral side 120 (seen in FIG. 1A) and lateral sides 122 are attached at the broad face's sharpened junction with the elongated body of the instrument 100; and, noted is the more proximal position of the narrow face 118 (at the distal end) with respect to the instrument 100.

The proximal end 112 (shown in FIGS. 1A, 1B, 2A) terminates with the broad, narrow, counter-lateral and lateral sides 116, 118, 122, 120 orthogonal, or more acutely angled, with respect to the longitudinal axis of the instrument 100.

The size of the instrument 100 may vary in length, width and height. The blade portion 117 may vary in dimension and may depend on the size (width) of the instrument 100. The blade portions 117a-c described herein may further include curved sides which project from the elongate body 110 of the instrument 100, or one curved side and a straight side which form each of the blade portions 117a-c.

Figure 3A:
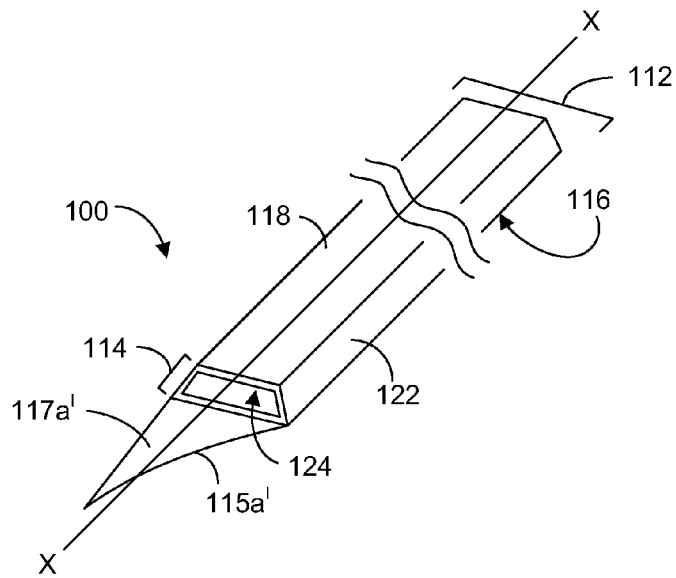
FIG. 3A provides a perspective view of an embodiment of a medical instrument comprising a hollow elongate body and a blade projecting distally from the broad face.

FIG. 3A provides a perspective view of a hollow medical instrument embodiment 100 which can be used as a spinal needle, for example. The channel 124 is shown as extending from the distal end 114 of the instrument 100 to the proximal end 112, and the curved blade portion 117a' with cutting edge 115a' extending from the distal end of the broad face 116. The curved blade portion 117a' is provided with one curved side and one straight side projecting from the broad face 116 of the instrument 100.

Figure 3B:
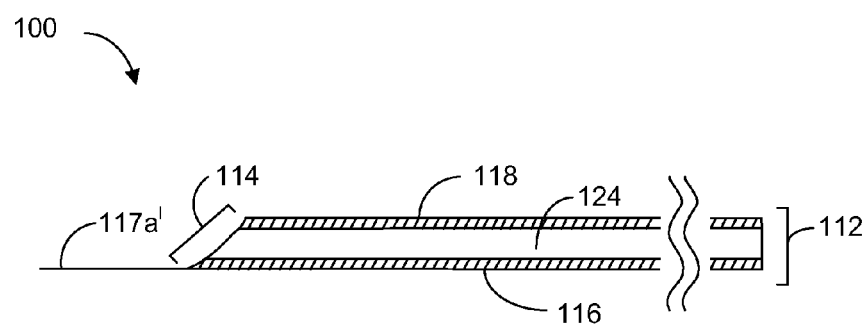
FIG. 3B provides a longitudinal cross-sectional view of the medical instrument embodiment of FIG. 3A taken at axis X-X.

FIG. 3B provides a longitudinal cross-sectional view of the embodiment of the medical instrument shown in FIG. 3A, taken at X-X, where the channel 124 can be seen as extending from the distal end 114 to the proximal end 112 with blade portion 117a'. The generally parallel narrow face 118 and broad face 116 are shown in the cross-sectional view. The channel 124 is configured to receive one or more medical components, said medical components comprising, for example, a fluid, a medication, a flat wire, a lead, a surgical instrument, a microchip, other medical or surgical tools among other components which may be introduced or extracted via the channel 124 of the instrument 100 into or from the body of the patient.

In some embodiments, in surgical operations, the cutting edge 115a' (shown in FIG. 3A) of the medical instrument 100 incises, or cuts into the surface of a tissue to create a linear opening in the tissue which is continued until the desired length and depth of incision is obtained. A stylet 154 (as shown below in FIGS. 12 and 14A), may be in place within the channel 124 of the instrument 100 to prevent tissue from being introduced into the channel 124 prior to introduction of the instrument 100 into the patient and before removal of the instrument 100 from the patient; or as desired during certain instrumentations.

FIG. 4A provides an embodiment of the instrument 100, however, in contrast to FIG. 3A, the blade portion 117d projects from the narrow face 118 of the instrument. The channel 124 is shown at the distal end 114, and it extends there through to the proximal end 112 of the instrument. The blade portion 117d may include a curved, jagged, or straight cutting edge 115d in the embodiments provided herein.

FIG. 4B is a longitudinal cross sectional view of the embodiment of FIG. 4A taken at axis X'-X' showing the channel 124 extending from the distal end 114 of the instrument 100 to the proximal end 112 with blade portion 117d extending from the narrow face 118 at the distal end 114. The channel 124 described herein may terminate at the distal end 114 of the instrument 100 as shown in some embodiments, wherein the opening of the channel 124 extends through the distal end 114 (FIGS. 1A-B, 2A-D, 3A-B, 4A-B).

FIG. 5: In other embodiments, the channel 124 may extend from an aperture 133 on the narrow or broad face 118, 116 (FIGS. 5A, B, C, D), or the lateral side (not shown) or counter-lateral side 122 of the instrument 100 to the proximal end 112 of the instrument 100. Therefore, in some embodiments, (as already previously shown) the medical instrument 100 is hollow.

Figure 5A:
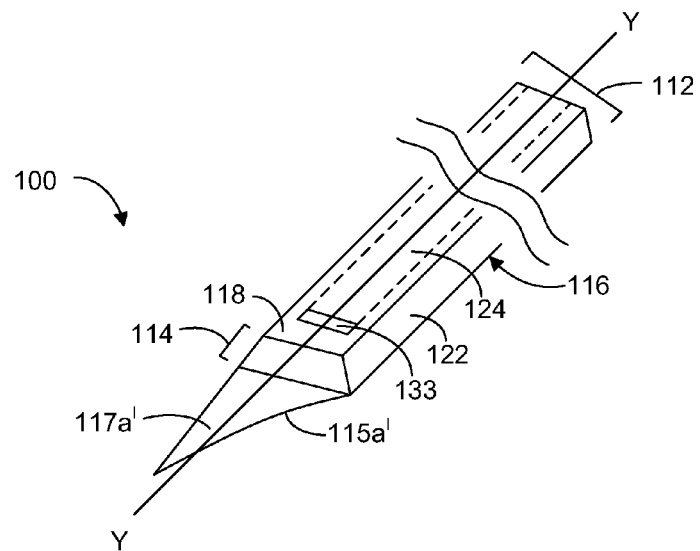
FIG. 5A provides a perspective view of another embodiment of a medical instrument with an aperture on the narrow face and a blade projecting distally from the broad side of the instrument.

In an embodiment, the channel 124 may extend from the proximal end 112 of the instrument 100 to an aperture 133 in the narrow face 118 as shown in FIG. 5A where the curved blade portion 117a' with cutting edge 115a' extends from the distal end 114 of the broad face 116.

Figure 5B:
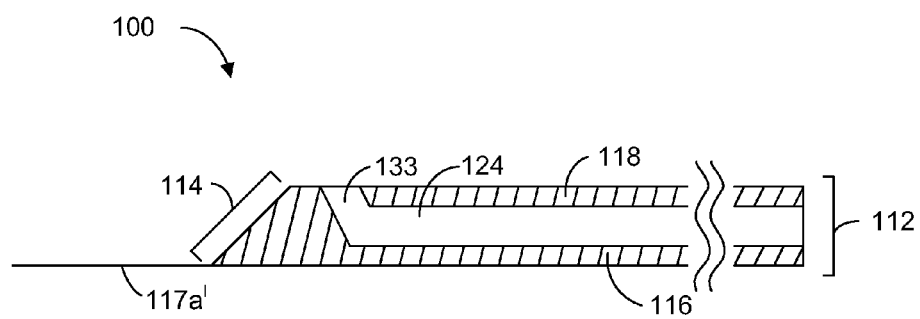
FIG. 5B provides a longitudinal cross-sectional view of the medical instrument embodiment of FIG. 5A taken at Y-Y.
Figure 5C:
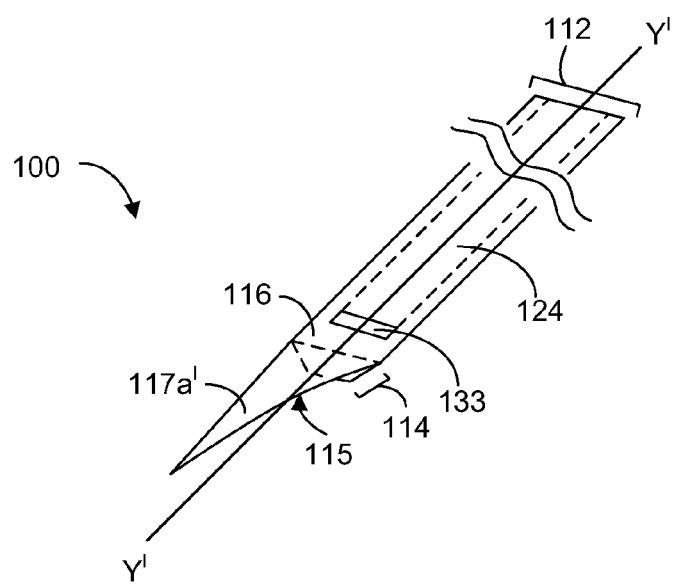
FIG. 5C provides a perspective view of a further embodiment of a medical instrument with an aperture on the broad face and a blade projecting distally from the broad side of the instrument.

In another embodiment, the channel 124 may extend from the proximal end 112 of the instrument 100 to an aperture 133 in the broad face 116 of the instrument 100 near the distal end 114 as shown in FIG. 5C. The blade portion 117a' extends from the distal end 114 of the broad face 116.

Figure 5D:
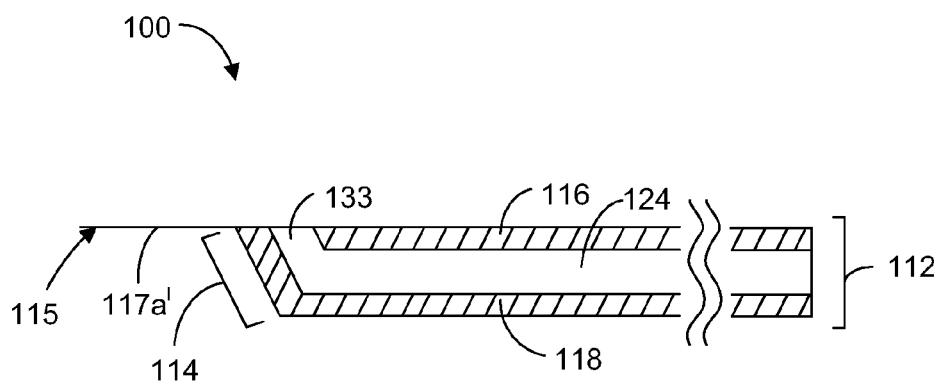
FIG. 5D provides a longitudinal cross-sectional view of the medical instrument embodiment of FIG. 5C taken at Y'-Y'.

FIGS. 5B and 5D provide longitudinal cross-sectional views of FIGS. 5A and 5C, respectively. FIG. 5B shows the distal end 114 of the narrow face 118 is superior to and disposed proximal to the distal end of the broad face 116. FIGS. 5C and 5D show a 180 degree rotated version of the similar instrument as shown in FIGS. 5A-B, however FIGS. 5C-D include an embodiment of the instrument 100 with the aperture 133 in the broad face 116 instead of the narrow face 118 side (shown in FIGS. 5A-B). The aperture 133 may alternatively be provided in the lateral or counter-lateral sides 120, 122 of the instrument 100 (not shown in the Figures) as previously discussed, and may connect to the channel 124 which extends through to the proximal end 112. The aperture 133 allows for communication between the channel 124 of the instrument and the tissues or fluids of the body when the instrument 100 is in contact with the tissues or fluids and the stylet is removed.

Figure 6A:
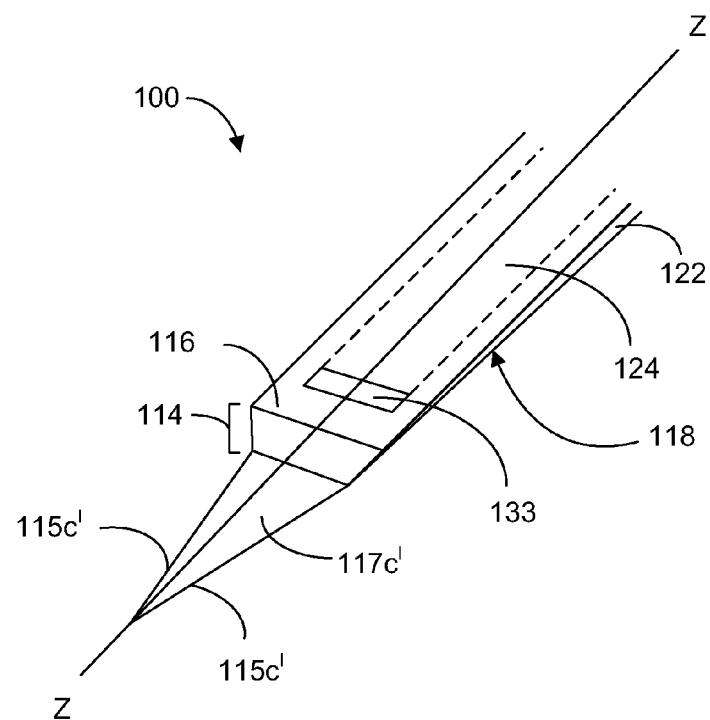
FIG. 6A provides a perspective view of a medical instrument embodiment including an aperture on the broad face and a blade extending distally from the narrow face.

FIG. 6A provides a perspective view of another embodiment of the instrument 100 wherein the broad face 116 includes an aperture 133 near its distal end 114, and the blade portion 117c' with cutting edges 115c' projecting distally from the narrow face 118. The channel 124 is shown as extending from the aperture 133 at the distal end toward the proximal end 112 (not shown in FIG. 6A). The lateral and counter-lateral sides 120, 122 are not parallel as shown in FIG. 6A.

Figure 6B:
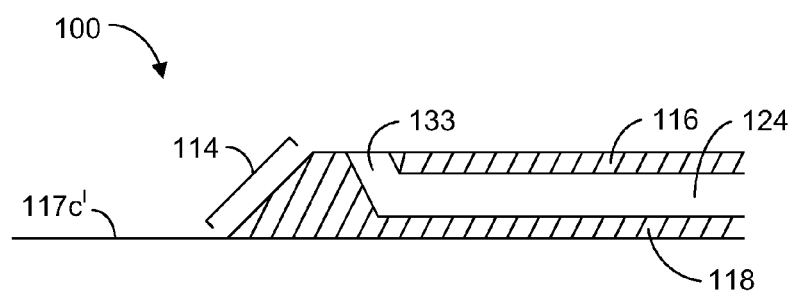
FIG. 6B provides a longitudinal cross-sectional view of the embodiment shown in FIG. 6A taken at Z-Z.

FIG. 6B provides a longitudinal cross-sectional view of FIG. 6A taken at axis Z-Z. The combination of the aperture 133 and the channel 124 when the instrument 100 is inserted into the patient's body provides access to various parts of the patient's body both above and below and on either side of the access point of the instrument 100. Benefits of this embodiment include the ability to introduce flat styli, flat wires, and other medical components (as will be shown in Figures described below) as well as to extract or insert fluids and tissue from/to the surrounding areas.

In one embodiment, the instrument 100 may be associated with a syringe, a suction device and/or a meter which may operate by use of the aperture 133 and the channel 124. In other embodiments the instrument 100 may be associated with a catheter device, a canula, an exit or input valve for gasses, for example.

FIG. 7A provides a top view of an epidural medical instrument embodiment 200 including a rounded or curved distal end 214. In some embodiments, as in the epidural needle embodiment 200, the channel 224 terminates at or opens to its distal end 214, and extends through the instrument 200 to the proximal end 212. The narrow face 218 is connected to the broad face 216 with lateral and counter-lateral sides 220, 222. A transverse cross-sectional view of the instrument 200 would reveal a trapezoid shape formed between the narrow and broad faces 218, 216, the counter-lateral side 222 and the lateral side 220 (as can be seen in FIG. 7C).

FIG. 7B provides a longitudinal cross-sectional view of FIG. 7A taken at axis Z'-Z' of FIG. 7A. The distal end 214 of the epidural instrument embodiment 200 is beveled or sloped as can be seen in FIG. 7B. The distal end 214 reveals a sharp cutting edge 215 for insertion into a target area of a patient. The distal end of the broad side 216 includes the cutting edge portion 215, and projects outward in a distal direction from the distal end 214 of the narrow face 218 of the epidural instrument 200. The cutting edge 215 is used to create an incision in a target area of a patient with the non-cutting, complimentary edge (i.e., narrow face 218 distal end 214) following behind the broad face 216 distal end 214 into the incision of the patient. The channel 224 shown in FIGS. 7B-7C extends from the distal end 214 to the proximal end 212 of the epidural instrument embodiment 200 as can be shown by the dashed line in the top view of FIG. 7A.

The distal end 214 of the broad face 216 includes a rounded sharpened edge shape, and the distal end 114 of the narrow face 218 includes a complimentary rounded edge shape. The distal ends 214 of the broad and narrow faces 216, 218 may or may not line up with one another at the distal end 214.

In FIGS. 7A-B the narrow face 218 distal end 214 does not include a cutting edge. However, in other contemplated embodiments, the entire distal end 214, or any portion thereof, (narrow or broad face, counter-lateral or lateral side) may include a cutting edge.

The distal end 214 of the broad and/or narrow face 216, 218 of the medical instrument 200 is rounded in shape when observed from the top or bottom of the instrument 200, and may have a 2:1, 3:1, or other ratio (broad: narrow), in some embodiments. The instrument 200 may have any modification of these shapes that confer a blade-like configuration and may contain a channel 224, and in some embodiments, a conforming stylet 154 for insertion therein (shown in FIG. 12). The embodiment of FIG. 7A can be visualized laterally (turned 90 degrees) as having a shape similar to that of a shark's mouth, and can be used with either the narrow face 218 or broad face 216 oriented in a superior position; or oriented laterally, relative to the other when inserting into the patient target area.

In ophthalmology a cataract can be removed and replaced with an intraocular lens (IOL) using the instrument described in FIG. 7A wherein the phacoemulsification and lens placement can be carried out by passing the varied ophthalmologic surgical instruments through and out of the channel 224 keeping the trapezoidal instrument in place, and thereby avoiding the stress and over manipulation of eye tissue.

Figure 8:
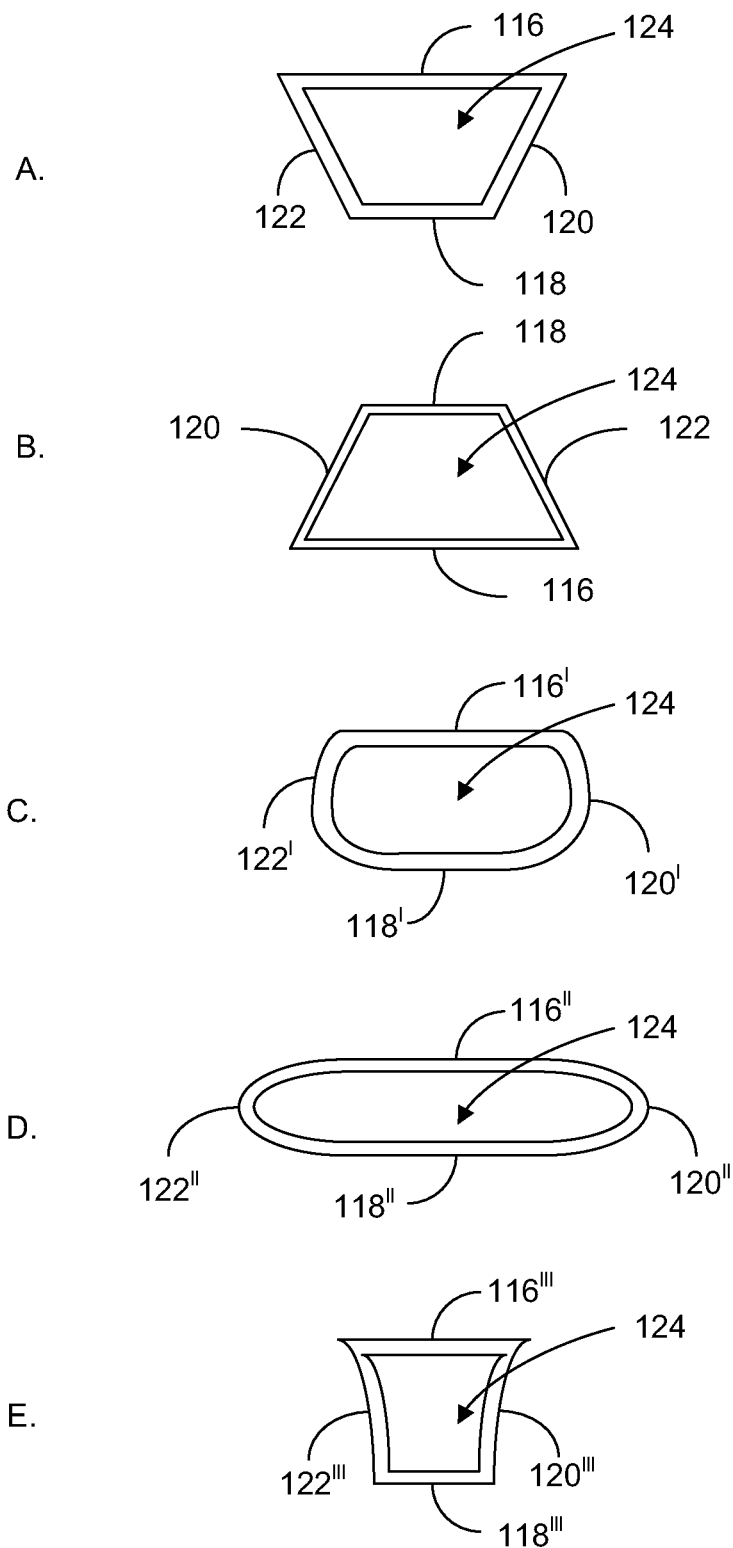
FIGS. 8A-E provide various examples of cross-sectional views of embodiments of the medical instrument according to the invention.

FIGS. 8A-E provide examples of transverse cross-sectional views of various embodiments of the medical instrument according to the invention. FIG. 8A provides a trapezoidal shape cross-section with the broad face 116 superior to the narrow face 118, and wherein the counter-lateral 122 and lateral sides 120 are not parallel to one another and the channel 124 is shown. FIG. 8B provides another embodiment of a trapezoidal shaped cross-section of an instrument wherein the narrow face 118 is superior to the broad face 116 and the counter-lateral and lateral sides 122, 120 are not parallel to one another and the channel 124 is provided. FIG. 8C is provided wherein the broad face 116' is flat and the narrow face 118' is curved such that the curved edges of the narrow face 118' connect to curved lateral and counter-lateral 120', 122' sides of the instrument, which also connect to the generally straight broad face 116, and the channel 124 is shown. FIG. 8D provides a further embodiment of an instrument wherein an ellipse shaped cross-section is provided with convex shaped lateral 120" and counter-lateral 122" sides and the channel 124 disposed there through. FIG. 8E provides yet a further embodiment, wherein the lateral and counter-lateral sides 120', 122'" are concave and connect between the broad and narrow faces 116'", 118'. The embodiments listed herein are for exemplary, non-limiting, purposes to show that additional shapes may be formed by the narrow and broad faces 118, 116, respectively, and the lateral and counter-lateral sides 120, 122, respectively, and the channel 124 of the invention described herein.

Figure 9:
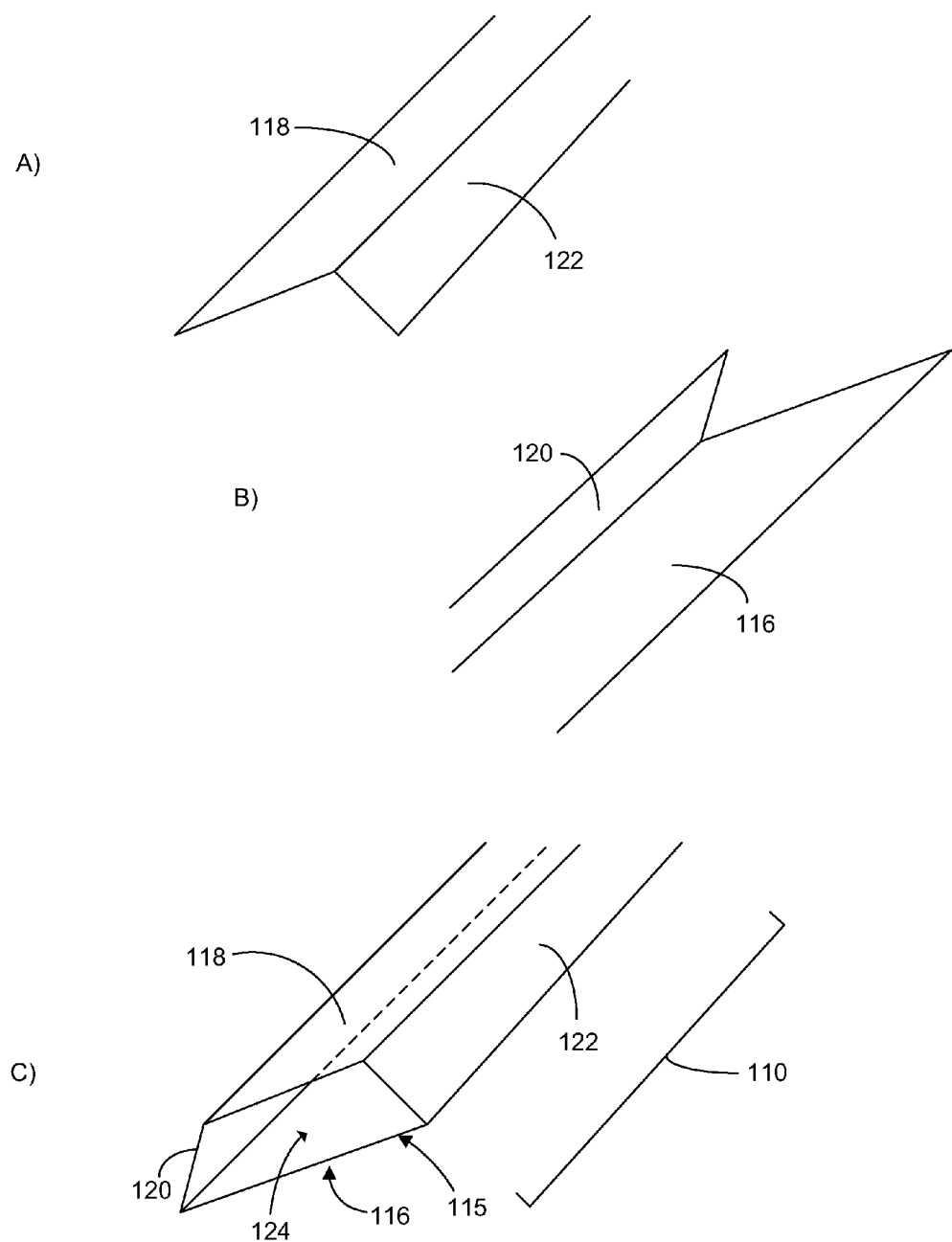
FIG. 9A provides a perspective view of a first portion of the construction of an embodiment of a medical instrument including a narrow face and a counter-lateral side joined at an angle, narrow-to-counter-lateral juncture.
FIG. 9B provides a perspective view of a second portion of the construction of an embodiment of a medical instrument including a broad face and a lateral side joined at an angle, broad-to-lateral juncture.
FIG. 9C provides a perspective view of an embodiment of the medical instrument, wherein the first and second portions of the medical instrument construction from FIGS. 9A and 9B are connected along the narrow face-to-counter-lateral side juncture and broad face-to-lateral side juncture of the embodiment to form the instrument, FIG. 9C.

FIG. 9A provides a perspective view of a first portion of an embodiment of a medical instrument including a narrow face 118 and a counter-lateral side 122 joined together at the junction angle disposed.

FIG. 9B provides a perspective view of a second portion of an embodiment of a medical instrument, including a broad face 116 and a lateral side 120 joined at the junction angle disposed.

FIG. 9C provides a perspective view of an embodiment of the medical instrument, wherein the first and second portions from FIGS. 9A and 9B are connected such that the lateral side 120 connects to the narrow face 118 and the broad face 116 connects to a counter-lateral side 122 as the two components are united to form the trapezoid figure.

FIGS. 9A-C are provided to demonstrate the ease with which an embodiment of the medical instrument 100 can be constructed during a manufacturing process. Two portions can be connected to one another at two joints along the instrument to create the trapezoidal shaped elongate body 110 including the cutting edge 115 and the channel 124 disposed there between. This example provided is only one example of a method which can be used to create the instrument(s) described herein. There are numerous other ways to create and configure the medical instrument(s) embodied in the disclosure herein.

FIG. 10A provides a construction example using material product, e.g. steel sheet (cross section), for a first portion (A) and a second portion (B) of a medical instrument.

FIG. 10B provides a view of the first portion (A) being manipulated such that its ends are conformed to meet the second portion (B) thereby forming the narrow face 118, the counter-lateral side 122 and the lateral side 120 of the instrument which can then be connected to the second portion (B) which forms the broad face 116 of the instrument.

FIG. 10C provides a view of the medical instrument formed by the first portion and second portions of FIGS. 10A-10B, wherein the point at which (A) contacts (B), (A) and (B) are secured to one another by conventional methods known to the industry to form the medical instrument embodiment revealing the narrow face 118, broad face 116, lateral side 120 and counter-lateral side 122.

Figure 11:
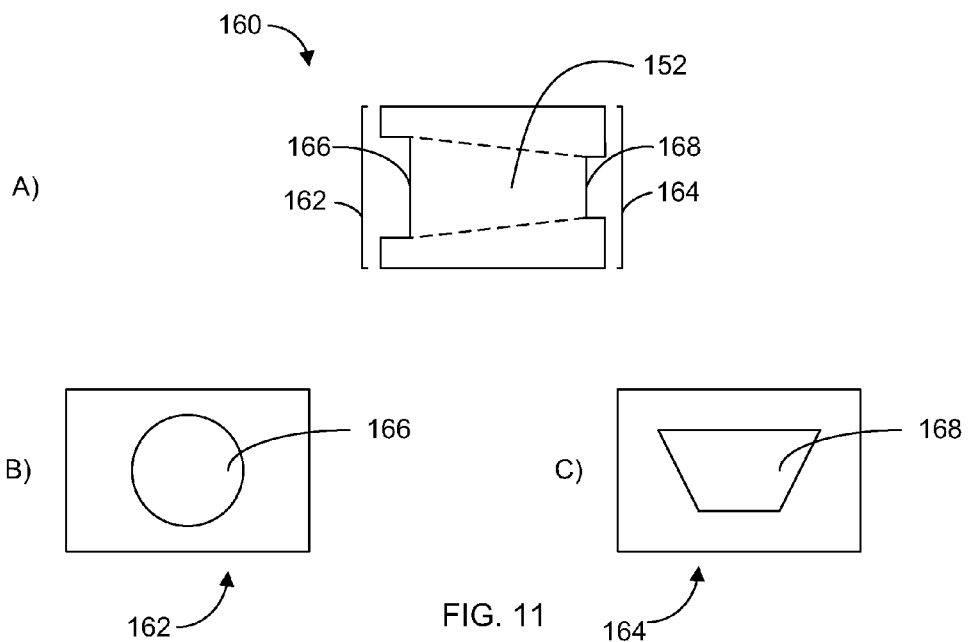
FIG. 11A provides a side view of an adapter according to an embodiment of the instrument including a distal end (for insertion of foreign or round input source to the adapter) and a proximal end (for insertion of the instrument or a portion thereof).
FIG. 11B provides a cross-section distal fitting view of the adapter at in FIG. 11A.
FIG. 11C provides a cross-section proximal fitting view of the adapter in FIG. 11A.

FIG. 11A provides a side view of an adapter 160 for use in conjunction with the instrument to make conventional component inputs compatible with the trapezoidal form, according to one embodiment. The adapter 160 further includes a communicating channel 152, connecting between the first opening 166 (non trapezoidal) and the second opening (trapezoidal) 168.

FIGS. 11B and C provide end views of the adapter 160, wherein the first opening 166 non-trapezoidal end is shown in FIG. 11B, and the second opening (trapezoidal) 168 end is provided in FIG. 11C.

The adapter 160 has a proximal end 162 and a distal end 164, which are configured to accommodate, or fit, a standard size and shape of a tubing currently found in the prior art. The adapter 160 can provide communication via the communicating channel 152, between the instruments and medical components typically found in hospitals and clinics (i.e., round-ended components and instruments), and the subject medical instrument 100.

Figure 12:
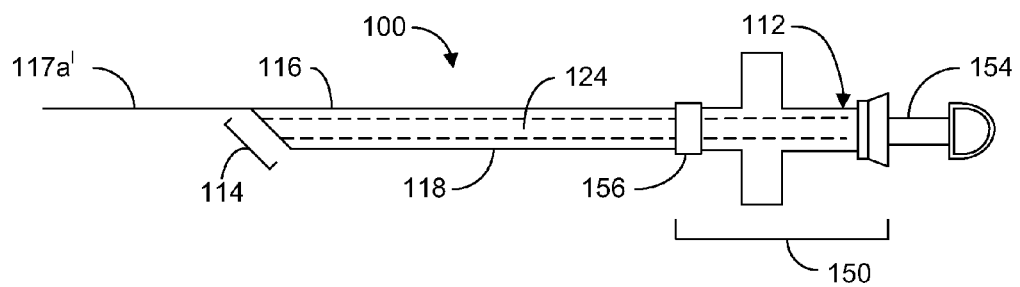
FIG. 12 provides a side view of an embodiment of the medical instrument including a handle and a stylet at the proximal end.

FIG. 12 provides a side view of an embodiment of the medical instrument 100, wherein a handle component 150 is attached thereto. The handle component 150 may be used to introduce or to remove the medical instrument 100 to and/or from the subject during use. Furthermore, the handle component 150 can be used to manipulate the medical instrument 100 within the body of the subject. The handle component 150 may take any shape or size known to those of skill in the art; the handle component 150 as shown in FIG. 12 is provided for example, only, and not intended to be limiting. Additional features may be included on or associated with the handle component 150 including but not limited to: movement controls, suction features, valves, location and proximity sensors, temperature sensors, cameras, and the like may be used to enhance the performance of the medical instrument 100 during a procedure. The handle component 150 may attach to a connection component 156 at the proximal end 112 of the medical instrument 100. This connection component 156 may also be configured to connect to a syringe, for example, or any other adaptable device. A stylet 154 is shown as being inserted into the instrument 100 through the connection component in FIG. 12. A stylet 154 may be inserted into the longitudinal channel 124 with or without a handle component.

The stylet 154 may also include, facilitate and support numerous functions and components such as sensors, cameras, illuminators, and/or electrodes, for example, to provide feedback of the location of the instrument 100 within the patient or target area, among other information, and other conventional uses in applications of the art.

To effect the introduction of a fluid, for example, using the medical instrument 100, the stylet 154 is withdrawn. A fluid pressure is imposed internally within the longitudinal channel 124 by a syringe or pump, or mechanical device which can be connected and applied at the proximal end 112. The internal fluid pressure created within the channel 124 may be thereby discharged into the internal tissues, organ, body cavity, or vessel. The stylet 154 may operate in the traditional manner of syringe suction to withdraw fluids from a vial or vein, for examples, and, conversely, impose pressure in the syringe to release the contents into the target area.

Figure 13:
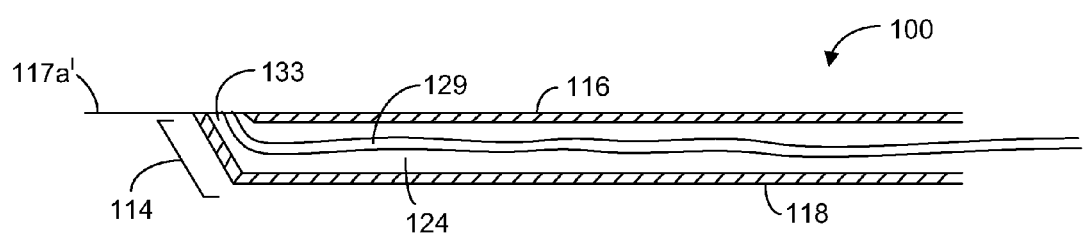
FIG. 13 provides a side cross sectional view of an embodiment of a medical instrument providing an aperture for the channel, a cutting edge, and the longitudinal channel terminating distally and diverted angularly through the aperture.

A surgical instrument, wire, flat lead, microchip, camera and light, or other medical component or device can be deployed through the medical instrument 100 once the stylet 154 is removed. The medical components or devices are inserted straight through the proximal end 112 to the distal end 114 of the channel 124 into the target area of the patient, for example. In some embodiments, the channel 124 of the medical instrument 100 may not open to the distal end 114 of the instrument 100 as shown in FIG. 13. However, in these embodiments, the aperture 133 provides communication between the channel 124 and the body or tissue or anything outside of the instrument 100. The channel 124 and aperture 133 combination provides the ability to travel and communicate further into and at a varying angle through the body of the patient. This may be possible with a medical component inserted through the instrument 100 via the channel 124 and aperture 133. More than one aperture 133 may be provided in any of the embodiments and surfaces contemplated herein.

The aperture 133, which may be rectangular or other shapes, at the surface of the instrument 100 communicates orthogonal to, or at an angle to the channel 124 axis for injections, extractions, or placement of instruments or other devices. These devices, wires, flat leads, or instruments can be removed from the external tissue or fluids by backing them out through the aperture 133 and being continuously withdrawn through the channel 124 through to the proximal end 112.

Once the procedure is complete, the stylet 154 may be replaced within the medical instrument 100 to block the aperture, or opening, and the medical instrument 100 may be carefully withdrawn from the linear incision site.

The medical instrument 100 can be used with, in one embodiment, the broad face 116 facing up, superior, or the narrow face 118 facing up, superior for entering any body tissue or cavity. For example, in a venipuncture procedure, the narrow face 118 of the medical instrument 100 can be maintained in the upper position and be posterior, more proximal, relative to the broad face 116 cutting edge 117a' to facilitate visualization (FIG. 12).

To effect the extraction fluids or tissue (e.g. biopsy, liposuction) the medical instrument 100 may be used, wherein the instrument 100 may not include any apertures 133 other than the channel 124 seen in FIGS. 2B, 3A, 7A, 7B, and 12.

The retrograde passage of fluids, tissue, or detritus from the distal most channel 124, opening 133, leads to the channel 124, and flows along the longitudinal axis to the proximal 112 end of the channel 124. This may be accomplished by application of devices such as forceps, by suction, syringe, or external pump mechanism, for example. Where the pressure gradient is greater in the tissue or surrounding fluids the flow would advance through the channel 124 passively without the requirement of a suctioning device at the proximal end 112 of the instrument 100.

FIG. 13 provides a longitudinal cross-sectional view of the medical instrument 100 according to an embodiment of the invention, wherein the channel 124 and aperture 133 are illustrated.

To introduce a wire or lead 129 may disposed within the channel 124 of the instrument 100 as shown in FIG. 13. Fluid, air, gas, medicaments, sensors, electrical wires and leads, and any other such devices may be passed through the channel 124 and through the aperture 133 orthogonally or at an angle as can be seen in FIG. 13. The removal of instruments has previously been cited.

FIG. 14: as can be seen in the embodiments of FIGS. 14A-D, a design advantage of the medical instrument 100 having a broad face 116, narrow face 118, distal end 114, and proximal end 112, is that it may provide the ability to pass a stylet 154, medical components such as scissors, retrieving instruments as well as cameras, sensors, pacemakers, stents, and illuminators and other medical components through long axis of the instrument 100. The structure of the instrument 100 described herein provides greater latitude for any instruments and devices requiring moving parts.

FIG. 14A provides a perspective view of a medical instrument 100 according to an embodiment of the invention wherein a trapezoidal-shaped stylet 154 at the proximal end 112 is disposed within the medical instrument 100. The trapezoidal stylet 154 may also include or embody numerous functions and components such as sensors, cameras, illuminators, and electrodes, for examples, to provide feedback about the location of the instrument 100 within the patient, among other information.

FIG. 14B provides a perspective view of the medical instrument 100, wherein a circular conduit or circular shaped device 924 is inserted from the proximal end 112 through to the distal 114 end of the medical instrument 100.

FIG. 14C provides a perspective view of a medical instrument 100 according to an embodiment of the invention, wherein two conduits or circular-shaped devices 925a, 925b are inserted from the proximal end 112 through to the distal end 114 of the medical instrument 100. The embodiment shown in FIGS. 14B, 14C, are not meant to be limiting as multiple conduits or circular-shaped devices 925a, b, can be inserted through the instrument 100, while only two are shown in the embodiment of FIG. 14C.

The embodiments of FIGS. 14B and 14C demonstrate that various shaped devices commonly found in the art can be inserted through the instrument 100 of the subject invention, including but not limited to circular-shaped devices which are commonly found in the medical industry.

US Patent Publication No. 20040111020A1, by Gary Long, demonstrates the use of a flexible member for advancing in the body of a patient which allows for the passage of other components such as a camera, a light source, and a vacuum opening there through. The circular component(s) 924, 925a, and 925b in FIGS. 14B and 14C may have openings there through which to provide a similar function as that provided in the Long Patent Publication.

Devices such as scissors, forceps, fluid, air, gas, or medicament supply conduits, cannulas, electrical wires and leads, and any other such devices may also be passed through the conduits 924, 925a-b. These devices and other related medical components may also be passed through the hollow trapezoidal shape of the medical instrument 100.

FIG. 14D provides a perspective view of a medical instrument 100 according to an embodiment of the invention, wherein a trapezoidal-shaped device 926 having two openings 927 is inserted into the medical instrument 100. The device 926 which includes a trapezoidal shape complementary to that of the inside dimensions of the instrument 100, can be passed through or provided within the hollow opening of the instrument 100, including openings 927 wherein these may extend through the entire device 926. The openings may allow the passage of other medical components such as those already described in FIGS. 14A, B, and C.

Figure 15A:
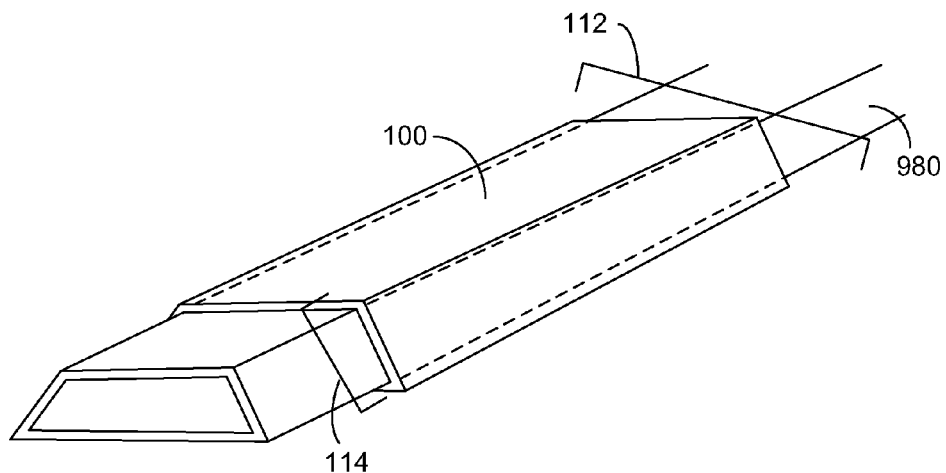
FIG. 15A provides a perspective view of a medical instrument according to an embodiment of the invention, including a trapezoidal catheter, which is inserted through the opening of the medical instrument from the proximal end to the distal end of the medical instrument and into the target area.

FIG. 15A provides a perspective view of a medical instrument 100 according to an embodiment of the invention, including a catheter 980 which is inserted through the trapezoidal shaped opening of the medical instrument 100 from the proximal end 112 to the distal end 114 of the medical instrument once the instrument 100 has entered the target area.

Figure 15B:
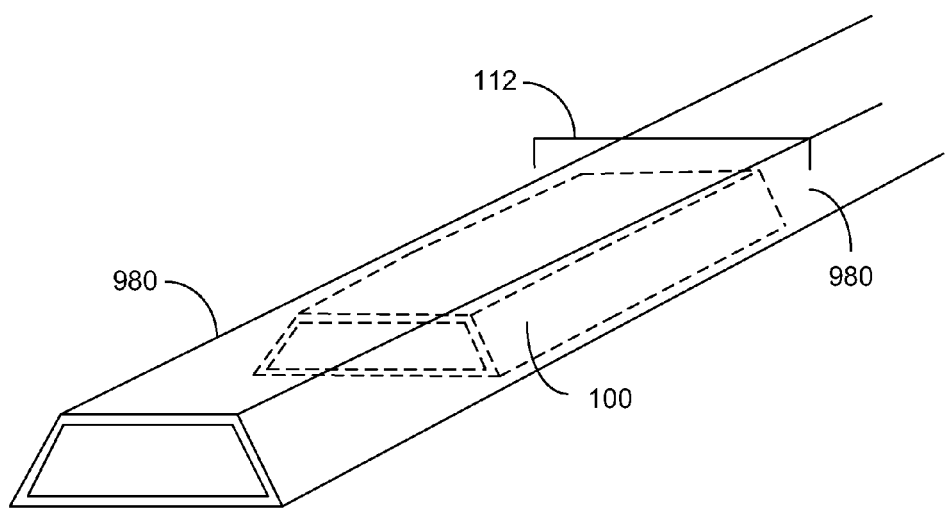
FIG. 15B provides a perspective view of a medical instrument where a catheter is advanced, or slid, over the instrument, as a covering sleeve, to penetrate into the body of the target area.

FIG. 15B provides a perspective view of a medical instrument 100 wherein a catheter 980 may be provided and advanced over the outside of the medical instrument 100, as a sleeve, such that the catheter 980 can be introduced into the body of a patient when the instrument 100 is being introduced into the target area. The instrument 100 could then be withdrawn. Instruments, flat wires, microchips, flat metal plates, visual imaging tools and devices can be advanced through the catheter to the desired location to carry out their purpose and function as described in the Publication WO2005113056A2 by Bakos et al, using a guide wire. These techniques can also be adaptable for use with the subject medical instrument 100. The catheter can remain in situ, in place, for use as an intermittent or continuous infusion of anesthetics, medications, nutrients, intravenous hydration or for other therapeutic purposes such as drainage of fluids (hemothorax) or gases (pneumothorax), for example. Other configurations for purposes not envisioned in the above descriptions are nevertheless implied by the general principles outlined above.

The instrument 100 of the present invention can be used in many medical procedures, including but not limited to epidural, spinal procedures, tracheotomy, thoracotomy, and conditions such as hemothorax, pneumothorax, and in arthroscopy, arthrotomy, and liposuction. Catheter sleeves have been used in the prior art with guidewires to aid in the introduction of the catheter and other instruments into many sites in the human body as in Patent Publication WO2005113056A2, J. Gregory Bakos et al, for example.

The instrument 100 may further be beneficial over the prior art in gaining access to virtual cavities, anatomical cavities, arteries, veins, collections of fluid, biopsy, catheterizations, bloat in animals, laparoscopic surgeries, passing diagnostic wires and flat leads, antibiotic and chemotherapy delivery. Linear incisions are preferred over conventional pyramidal or conical penetrating instruments, because it allows for more rapid and efficient healing once the procedure has terminated. Withdrawal of the medical instrument 100 from the patient leaves the linear incision site with no evidence of puncture and no tissue damage on entry or entrained upon removal. The medical instrument's 100 conforming catheter 980 can be removed through the original incision site without incident damage to tissues.

Materials and Methods

Materials:

The medical instrument described in embodiments herein may be made by the conventional methods used in the metal arts, including for example, drawing, roll forming, slitting, forging, laser and seam welding, swaging, beveling, and polishing. The existing materials in use for medical devices such as Stainless steel and similar alloys which are suitable for their corrosion resistance, strength and ductility may be employed in some embodiments. Since conventional tubular needles and Trocar devices are generally made by rolling up of flat sheet into a round configuration and seam welding, the embodiments of medical instruments described herein would use the same materials but shaped differently before seam welding. Thus, no radical departure from conventional construction methods of prior art needles is needed.

The critical requirements of materials for use in the body are corrosion resistance, low toxicity, ductility and elasticity such that no breakage can occur internally and no chemical transfer to body fluids or tissues is possible. Another key requirement is the ability to withstand sterilization methods involving heat or fluids without changes in properties or surface characteristics. The materials should not be porous or easily scratched or prone to fracture. Thus, ceramic materials, while having many desirable characteristics for this design suffer from low ductility. However, these materials may be used in the embodiments herein. Some of the preferred materials meeting these restrictions, for example, include 304 Stainless Steel, 316 Stainless Steel, 15-5 PH Stainless Steel, Titanium-6-4, the new amorphous alloy compositions particularly such as Zr/TI produced by Liquid-Metal Technologies. The later material has a high elastic strain limit, a strength superior to stainless steels and exceptional corrosion resistance. It is currently used in other medical applications and can be injection molded like a plastic. These examples as well as other materials known to those of skill in the art are contemplated within the subject disclosure.

Methods:

The configurations described herein and those contemplated by the disclosure herein can be constructed by two principal methods. The first method is similar to the conventional hypodermic tube fabrication, a roll forming operation of coil strips (steel) in appropriate thickness of sheet material is subjected to incremental longitudinal bends until the desired cross section (trapezoid) profile is obtained. The second method includes Roll forming of coil strips (steel) in appropriate thickness of sheet material makes one incremental angle bend of 45 degrees to a first longer width that represents the broad surface of the trapezoid form. A separate incremental angle bend of 135 degrees is made to a second shorter width that represents the narrow surface of the trapezoid form. There may be a ratio of 2:1, 3:1, or other ratio between the two (broad/narrow or narrow/broad) faces, for example. The two angled strips are enjoined together, welded by Heli-Arc or laser to form the trapezoid (see FIGS. 8A-C for example). The broad face may include 45 degree angles at each end, and the narrow face may include contain the 135 degree corresponding angles in these embodiments remaining to form the trapezoid cavity. The degree of angles can be increased or decreased depending on the specifications required.

In another method, an alloy powder is injection molded to the desired cross section and the pre-form is sintered to form the solid body. Formation of a tip is done by mechanical processing by conventional metal working operations.

Additionally, the point or tip of the trapezoid flat blade needle can be created from the trapezoid stock used by cutting, i.e. undercutting the broad surface along the longitudinal axis of the flat blade to a desired depth of tip. The remaining lateral sides that formed the trapezoid with the distal narrow surface can be cut back orthogonal, or at an angle, from the end point of the cut made beneath the broad plane and sealed in one embodiment.

Moreover, in one embodiment, the distal tip of the instrument can be made from a metal blank of proper gauge and characteristics to be laser welded, or by other common processes known to the metal industry, continuous with the broad surface's distal end of the medical instrument. The lateral sides and narrow surface distal end can be sealed by laser welding such that an opening for the distal end of the channel can be created.

It is possible to construct an alternative blade tip that would fit into an area that is cut away from the trapezoid stock's broad distal surface of the needle to accommodate the gauge and form of cutting blade.

Finally, while various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference in their entirety to the extent they are not inconsistent with the teachings herein.

What is claimed is:

1. A medical instrument for insertion into a subject, comprising an elongate body comprising a proximal end and a distal end, a broad face, a narrow face, a lateral side and a counter-lateral side, the broad and narrow faces being linear and parallel to one another, and said later and counter-lateral sides each spanning between the broad face and narrow face, and a triangular blade extending from the distal end, the blade comprising a blade bottom surface that extends distally from and is co-planar to the broad face wherein the distal end comprises a slope between the broad face and the narrow face, wherein a longitudinal channel is disposed between the broad face, narrow face, lateral side and counter-lateral side of the medical instrument, wherein the distal end of at least one of the broad and narrow faces comprises a cutting edge and wherein the broad face comprises opposing edges that are linear and parallel from the distal end to the proximal end and the narrow face comprises opposing edges that are linear and parallel from the distal end to the proximal end.

2. The medical instrument of claim 1, wherein the lateral and counter-lateral sides are not parallel to one another, such that said broad face, narrow face, lateral side and counter-lateral side together form a trapezoid shape there between.

3. The medical instrument of claim 1, wherein said instrument is configured to associate with a catheter device, a syringe, a suction device, a stylet and/or a meter.

4. The medical instrument of claim 1, wherein the channel is configured to receive one or more medical components, said medical components comprising a medication, a flat wire, a lead, a surgical instrument, and/or a microchip.

5. The medical instrument of claim 4, wherein the channel extends from an aperture on the broad face, narrow face, lateral side or counter-lateral side of the instrument to the proximal end of the instrument.

6. The medical instrument of claim 4, wherein the medical instrument is configured to introduce the medical components into and/or remove the medical components from the subject.

7. The medical instrument of claim 1, wherein the channel extends from the distal end to the proximal end of the medical instrument.

8. The medical instrument of claim 1, wherein the height to width ratio of a cross-section of the elongate body ranges from 1:2 to 1:15.

9. The medical instrument of claim 8, wherein the height to width ratio of a cross-section of the elongate body comprises 1:2, 1:3, 1:4, 1:5, 1:6, 1:7, 1:8, 1:9, 1:10, 1:11, 1:12, 1:13, 1:14, or 1:15.

10. The medical instrument of claim 1, wherein the needle comprises an epidural needle or a spinal needle.

11. A medical instrument for insertion into a body of a subject, said instrument comprising a proximal end, a distal end, a broad face, a narrow face, a lateral side and a counter-lateral side, each of the broad and narrow faces comprising a first end and a second end, said broad and narrow faces are parallel to one another and said broad face comprises a greater width than said narrow face, and a triangular cutting edge extending from the distal end, the cutting edge comprising a bottom surface that extends distally from and co-planar to the broad face wherein the distal end comprises a slope between the broad face and the narrow face, wherein the lateral and counter-lateral sides are disposed between the broad and narrow faces, such that one of said lateral and counter-lateral sides connects the first end of the broad face to the first end of the narrow face and the other of the lateral side and the counter-lateral sides connects the second end of the broad face to the second end of the narrow face to form a trapezoidal shape between the broad face, narrow face, lateral side and counter-lateral side, wherein said lateral and counter-lateral sides are not parallel to one another, and wherein the broad face comprises opposing edges that are linear and parallel from the distal end to the proximal end and the narrow face comprises opposing edges that are linear and parallel from the distal end of the proximal end.

12. The medical instrument of claim 11, wherein the broad and narrow faces, and lateral and counter-lateral sides connect to form a channel through the medical instrument from the proximal end of the instrument to the distal end of the instrument, said channel configured to receive one or more medical components, said medical components comprising a medication, a fluid, a tissue, a flat wire, a lead, a surgical instrument, and/or a microchip.

13. The medical instrument of claim 12, further comprising an aperture in the broad face, narrow face, lateral side and/or counter-lateral side, wherein the channel connects between the aperture and the channel of the instrument, said aperture is configured to receive or pass one or more medical components, said one or more medical components comprising a medication, a flat wire, a lead, a surgical instrument, and/or a microchip.

14. The medical instrument of claim 13, wherein the aperture is disposed at the distal end of the instrument.

* * * * *